United States Patent
Wang et al.

(10) Patent No.: US 9,121,887 B2
(45) Date of Patent: Sep. 1, 2015

(54) HIGH MAGNETIC MOMENT PARTICLE DETECTION

(75) Inventors: Jian-Ping Wang, Shoreview, MN (US);
Chengguo Xing, Shoreview, MN (US);
Yuanpeng Li, Minneapolis, MN (US);
Balasubramanian Srinivasan, Saint Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 1131 days.

(21) Appl. No.: 12/712,989

(22) Filed: Feb. 25, 2010

(65) Prior Publication Data

US 2010/0213934 A1     Aug. 26, 2010

Related U.S. Application Data

(60) Provisional application No. 61/155,821, filed on Feb. 26, 2009, provisional application No. 61/236,689, filed on Aug. 25, 2009.

(51) Int. Cl.
*G01R 33/02* (2006.01)
*G01R 33/09* (2006.01)
(Continued)

(52) U.S. Cl.
CPC .............. *G01R 33/093* (2013.01); *B82Y 25/00* (2013.01); *G01B 1/00* (2013.01); *G01R 33/1269* (2013.01); *G01B 2210/00* (2013.01); *G01R 1/00* (2013.01); *Y10T 29/4902* (2015.01)

(58) Field of Classification Search
CPC ........ G01R 1/00; G01B 1/00; G01B 2210/00; G01B 2290/00; G01C 1/00; G01D 1/00; G01N 1/00; G01N 2201/00; G01N 2203/00

USPC ............... 435/287.2, 4–40.52, 287.1–288.7; 977/902–962; 324/251, 200, 207.22, 324/219, 228, 252, 260–263
See application file for complete search history.

(56) References Cited

U.S. PATENT DOCUMENTS 4,643,949 A * 2/1987 Kolycheck et al. ........ 428/425.9
5,981,297 A    11/1999 Baselt
(Continued)

FOREIGN PATENT DOCUMENTS

WO    WO-2008/072156 A2    6/2008
WO    WO-2009/013658 A2    1/2009
(Continued)

OTHER PUBLICATIONS

"Giant magnetoresistance", Wikipedia, the free encyclopedia, [online]. [retrieved Jul. 5, 2010]. Retrieved from the Internet: <URL:http://en.wikipedia.org/w/index.php?title=Giant_magnetoresistance&01did=266082166>, (edited Jan. 24, 2009), 4 pgs.
(Continued)

*Primary Examiner* — Huy Q Phan
*Assistant Examiner* — Temilade S Rhodes-Vivour
(74) *Attorney, Agent, or Firm* — Schwegman Lundberg & Woessner, P.A.

(57) ABSTRACT

A device includes a sensor surface and a pair of electrodes. The sensor surface includes a first conductive layer separated from a second conductive layer by an intermediary layer, a magnetization direction of the first conductive layer and a magnetization direction of the second conductive layer having a ground state orientation of approximately 0 degrees. An electrical resistance between the pair of electrodes is determined by a magnetic field proximate the sensor surface.

34 Claims, 7 Drawing Sheets

(51) Int. Cl.
*G01B 1/00* (2006.01)
*B82Y 25/00* (2011.01)
*G01R 33/12* (2006.01)
*G01R 1/00* (2006.01)

(56) References Cited

U.S. PATENT DOCUMENTS

| | | | |
|---|---|---|---|
| 6,057,167 | A | 5/2000 | Shieh et al. |
| 6,291,993 | B1 * | 9/2001 | Fert et al. .................. 324/252 |
| 6,736,978 | B1 | 5/2004 | Porter et al. |
| 6,821,552 | B2 * | 11/2004 | Xu et al. ...................... 427/8 |
| 6,844,202 | B2 | 1/2005 | Prinz et al. |
| 7,391,091 | B2 * | 6/2008 | Tondra et al. ............ 257/427 |
| 7,463,021 | B2 * | 12/2008 | Steinich et al. ........ 324/207.13 |
| 7,626,384 | B2 * | 12/2009 | Hinz ......................... 324/252 |
| 7,736,891 | B2 * | 6/2010 | Nelson et al. ............. 435/288.5 |
| 8,063,634 | B2 * | 11/2011 | Sauber et al. ............. 324/252 |
| 8,102,175 | B2 * | 1/2012 | Rossler et al. ............ 324/252 |
| 8,143,886 | B2 * | 3/2012 | Huet et al. ................ 324/258 |
| 2006/0128035 | A1 * | 6/2006 | Coehoorn et al. ........ 436/524 |
| 2006/0292630 | A1 * | 12/2006 | Fukumoto ................. 435/7.1 |
| 2007/0170913 | A1 * | 7/2007 | Yokotani et al. ........ 324/207.22 |
| 2007/0254375 | A1 | 11/2007 | Tsukamoto et al. |
| 2008/0012558 | A1 * | 1/2008 | Rossler et al. ............ 324/252 |
| 2008/0054896 | A1 * | 3/2008 | Kahlman .................. 324/252 |
| 2008/0241822 | A1 * | 10/2008 | Wyrick et al. ............ 435/6 |
| 2008/0284419 | A1 | 11/2008 | Ikeda |
| 2008/0309329 | A1 | 12/2008 | Kahlman et al. |
| 2009/0072815 | A1 | 3/2009 | Kahlman et al. |
| 2009/0086358 | A1 * | 4/2009 | Van de Veerdonk et al. ... 360/55 |
| 2009/0102465 | A1 | 4/2009 | Jansen et al. |

FOREIGN PATENT DOCUMENTS

| | | |
|---|---|---|
| WO | WO-2009/013662 A1 | 1/2009 |
| WO | WO-2009/013668 A2 | 1/2009 |
| WO | WO-2009/040712 A2 | 4/2009 |
| WO | WO-2009/053902 A2 | 4/2009 |
| WO | WO-2010/098884 A1 | 9/2010 |

OTHER PUBLICATIONS

"International Application Serial No. PCT/US 2010/000605, Written Opinion mailed Jul. 8, 2010", 7 pgs.

"International Application Serial No. PCT/US2010/000605, International Search report mailed on Jul. 8, 2010", 4 pgs.

Anderson, N. L., et al., "The Human Plasma Proteome", *Molecular & Cellular Proteomics*, 1.11, (2002), 845-867.

Baselt, D. R., et al., "A biosensor based on magnetoresistance technology", *Biosensors & Bioelectronics*, (1998), 731-739.

De Palma, R., et al., "Magnetic Bead Sensing Platform for the Detection of Proteins", *Anal. Chem.*, 79, (2007), 8669-8677.

Fert, A., "Origin, Development, and Future of Spintronics", *Angw. Chem. Int. Ed.*, 47, (2008), 5956-5967.

Fullerton, E. E., et al., "The 2007 Nobel Prize in Physics: Magnetism and Transport at the Nanoscale", *ACS Nano*, 1(5), (2007), 384-389.

Gomez, M., et al., "Lung Cancer Screening", *Am. J. Med. Sci.*, 335(1), (2008), 46-50.

Graham, D. L., et al., "Magnetoresistive-based biosensors and biochips", *TRENDS in Biotechnology*, 22(9), (2004).

Janssen, X. J. A., et al., "On-chip manipulation and detection of magnetic particles for functional biosensors", *Biosensors and Bioelectronics*, 23, (2008), 833-838.

Lagae, L., et al., "On-chip manipulation and magnetization assessment of magnetic bead ensembles by integrated spin-valve sensors", *Journal of Applied Physics*, 91(10), (2002), 7445-7447.

Li, G., et al., "Spin valve sensors for ultrasensitive detection of superparamagnetic nanoparticles for biological applications", *Sensors and Actuators A—Physical*, 126, (2006), 98-106.

Macy, E. M., et al., "Variability in the measurement of C-reactive protein in healthy subjects: implications for referencee intervals and epidemiological applications", *Clinical Chemistry*, 43(1), (1997), 52-58.

Miller, M. M., et al., "A DNA array sensor utilizing magnetic microbeads and magnetoelectronic detection", *Journal of Magnetism and Magnetic Materials*, 225, (2001), 138-144.

Osterfeld, S. J., et al., "Multiplex protein assays based on real-time magnetic nanotag sensing", *Proc. Natl. Acad. Sci. USA*, 105(52), (2008), 20637-20640.

Prinz, G. A., et al., "Magnetoelectronics", *Science*, 282(5394), (1998), 1660-1663.

Sahab, Z. J., et al., "Methodology and Applications of Disease Biomarker Identification in Human Serum", *Biomarker Insights*, 2, (2007), 21-43.

Sandhu, A., "New probes offer much faster results", *Nature Technology*, 2, (2007), 746-748.

Shen, W., et al., "Detection of DNA labeled with magnetic nanoparticles using MgO-based tunnel junction sensors", *Applied Physics Letters*, 103, (2008), pp. 07A306-1-07A306-3.

Smith, C. H, et al., "Magnetic Biosensors", [Online] [archived on Oct. 27, 2004]. Retrieved from the Internet:: <URL: http://web.archive.org/web/20041027034142/http://www.sensorsmag.com/articles/1299/14_1299/main.shtml>, (Dec. 1999), 6 pgs.

Srinivasan, B., et al., "A Detection System Based on Giant Magnetoresitive Senors and High-Moment Magenetic Nanoparticles Demonstrates Zeptomole Sensitivity: Potential for Personalized Medicine", Angew. Chem. Int. Ed., 48, (2009), 2764-2767.

Tamanaha, C. R., et al., "Magnetic labeling, detection, and system integration", *Biosensors and Bioelectronics*, 24, (2008), 1-13.

Tondra, M., et al., "Model for detection of immobilized superparamagnetic nanosphere assay labels using giant magnetoresistive sensors", *J. Vac. Sci. Technol. A*, 18(4), (2000), 1125-1129.

"International Application Serial No. PCT/US2010/000605, International Preliminary Report on Patentability mailed Feb. 23, 2011", 11 pgs.

Kim, S., et al., "Optimizing the geometry of an in vitro tunneling magnetoresistance biosensor using an immobilized ferrimagnetic nanoparticle agent", *J. Appl. Phys.*, 104, (2008), 113911-1-113911-8 (8 pgs.).

Wang, S. X, et al., "Advances in Giant Magnetoresistance Biosensors With Magnetic Nanoparticle Tags: Review and Outlook", *IEEE Transactions on Magnetics*, 44(7),(Part 1), (2008), 1687-1702.

"European Application Serial No. 10708431.1, Office Action mailed Oct. 19, 2011", 2 pgs.

"European Application Serial No. 10708431.1, Response filed Apr. 30, 2012 to Office Action mailed Oct. 19, 2011", 18 pgs.

* cited by examiner

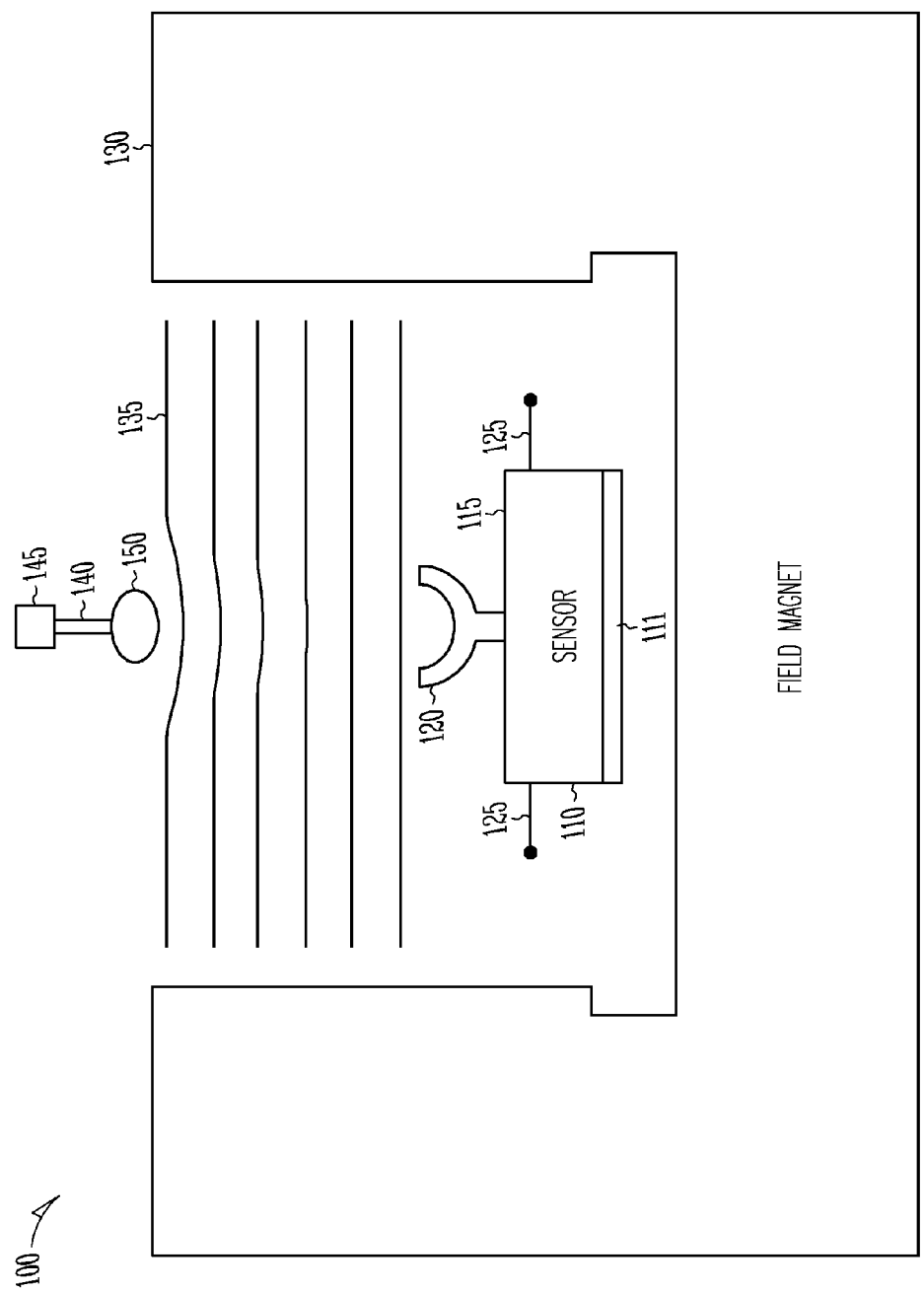

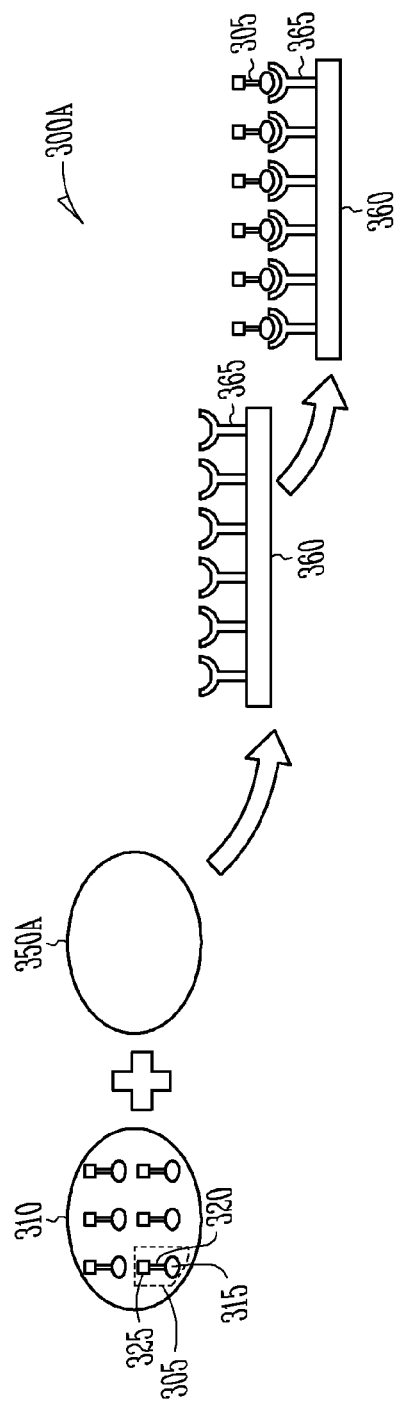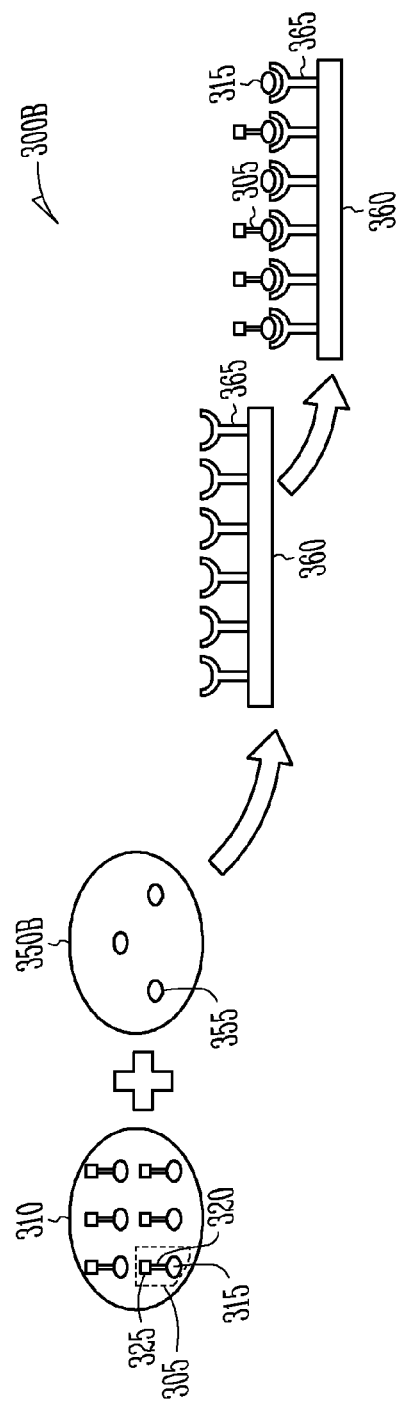

HIGH MAGNETIC MOMENT PARTICLE DETECTION

CLAIM OF PRIORITY

This patent application claims the benefit of priority, under 35 U.S.C. Section 119(e), to Jian-Ping Wang et al., U.S. Provisional Patent Application Ser. No. 61/155,821, entitled "GIANT MAGNETORESISTIVE SENSOR AND MAGNETIC NANOPARTICLE-BASED DETECTION SYSTEM," filed on Feb. 26, 2009 and to Jian-Ping Wang et al., U.S. Provisional Patent Application Ser. No. 61/236,689, entitled "HIGH MAGNETIC MOMENT PARTICLE DETECTION," filed on Aug. 25, 2009, both of which are incorporated herein by reference.

BACKGROUND

Present technology for detecting and quantifying biomedical molecules is inadequate. Detectors are too costly, complex, and not sufficiently sensitive.

OVERVIEW

Example 1 includes a device having a sensor surface and a pair of electrodes. The sensor surface includes a first conductive layer separated from a second conductive layer by an intermediary layer, a magnetization direction of the first conductive layer and a magnetization direction of the second conductive layer having a ground state orientation of approximately 0 degrees. An electrical resistance between the pair of electrodes is determined by a magnetic field proximate the sensor surface.

Example 2 includes the device of Example 1 and optionally wherein the ground state orientation is less than 60 degrees.

Example 3 includes the device of one or any combination of Examples 1-2 and optionally wherein the sensor surface is configured to detect proximity of a high magnetic moment particle.

Example 4 includes the device of Example 3 and optionally wherein the particles have a magnetic moment greater than 100 emu/g at room temperature.

Example 5 includes the device of one or any combination of Examples 3-4 and optionally wherein the particles have a magnetic moment that is seven times greater than that of magnetic oxide nanoparticles at 10 Oe magnetic field.

Example 6 includes the device of one or any combination of Examples 3-5 and optionally wherein the particles include high magnetic moment FeCo nanoparticles.

Example 7 includes the device of Example 5 and optionally wherein the nanoparticles are approximately 12 nm.

Example 8 includes the device of one or any combination of Examples 1-7 and optionally wherein the sensor surface and the pair of electrodes are integrated in a chip.

Example 9 includes the device of Example 8 and optionally wherein the chip includes a processor module configured to acquire data corresponding to the magnetic field.

Example 10 includes the device of one or any combination of Examples 1-9 and optionally including a magnetic field generator module configured to generate the magnetic field.

Example 11 includes the device of Example 10 and optionally wherein the magnetic field generator module is configured to generate two or more fields having a frequency in the range of 0 Hz to 1 MHz.

Example 12 includes the device of one or any combination of Examples 1-11 and optionally wherein the magnetic field is determined by a ratio of magnetic particle tagged binding partners to untagged binding partners.

Example 13 includes the device of one or any combination of Examples 1-12 and optionally wherein the sensor surface has a width of approximately 40 µm and a length of approximately 80 µm.

Example 14 includes the device of one or any combination of Examples 1-13 and optionally wherein the sensor surface has a ratio of length to width of less than 100.

Example 15 includes the device of one or any combination of Examples 1-14 and optionally wherein the sensor has a non-zero coercivity force.

Example 16 includes the device of one or any combination of Examples 1-15 and optionally wherein the electrical resistance as a function of the magnetic field exhibits hysteresis.

Example 17 includes the device of one or any combination of Examples 1-16 and optionally wherein the sensor surface includes a microfluidic channel.

Example 18 includes the device of one or any combination of Examples 1-17 and optionally wherein the sensor surface includes a container configured to receive a fluid sample.

Example 19 includes the device of one or any combination of Examples 1-18 and optionally wherein the sensor surface is part of at least one of a giant magnetoresistive (GMR) sensor, a magnetic tunneling junction (MTJ) sensor, an anisotropic magnetic (AMR) sensor, a giant magneto inductance (GMI) sensor, a Hall magnetic sensor, a magneto-optical sensor, or other sensor that provides an electrical output based on a change in magnetic field.

Example 20 includes the device of one or any combination of Examples 1-19 and optionally further including an interface to exchange data based on the electrical resistance with a remote device.

Example 21 includes the device of one or any combination of Examples 1-20 and optionally further including a notch in a perimeter of at least one of the first conductive layer or the second conductive layer, the notch configured to pin the magnetization.

Example 22 includes a method comprising exposing, adjusting, and determining. The method includes exposing a sensor surface to a magnetic field. Based on the magnetic field, the method includes adjusting magnetic direction alignment of a first layer relative to a second layer of the sensor surface. The first layer has a first magnetic direction and the second layer has a second magnetic direction, the first magnetic direction and the second magnetic direction have a ground state of approximately zero. Based on the adjusted magnetic direction alignment, the method includes determining an electrical resistance across the sensor surface.

Example 23 includes the method of Example 22 and optionally further includes affixing a binding partner to the sensor surface.

Example 24 includes the method of one or any combination of Examples 22-23 and optionally wherein adjusting the magnetic direction alignment includes determining a ratio of magnetic particle tagged binding partners to untagged binding partners.

Example 25 includes the method of one or any combination of Examples 22-24 and optionally further including communicating data corresponding to the electrical resistance to a remote device.

Example 26 includes a method of manufacturing a device comprising forming and immobilizing. The method includes forming a magnetic sensor having a plurality of layers. At least two of the layers are in at least one of substantially parallel alignment and substantially antiparallel alignment. The method includes immobilizing a first binding partner to a surface of the sensor. The first binding partner is configured to bind to a second binding partner. The second binding partner is coupled to a nanofabricated particle. The nanofabricated particle has a high magnetic moment and wherein the magnetic sensor provides an output based on detecting the nanofabricated particle proximate the surface.

Example 27 includes the method of Example 26 and optionally wherein forming the magnetic sensor includes forming a giant magnetoresistive sensor.

Example 28 includes the method of one or any combination of Examples 26-27 and optionally wherein immobilizing a capture antibody, a DNA strand, an RNA strand, a small molecule, a peptide, an aptamer, or a multiplex biomolecule to the surface.

Example 29 includes the method of one or any combination of Examples 26-28 and optionally wherein immobilizing the first binding partner includes immobilizing a capture oligonucleotide or polynucleotide to the surface.

Example 30 includes the method of one or any combination of Examples 26-29 and optionally wherein the second binding partner includes at least one of an antigen, a oligonucleotide, a polynucleotide, a pathogen, a protein, and a peptide.

Example 31 includes the method of one or any combination of Examples 26-30 and optionally further including providing a data communication channel between the output and a user perceivable display.

Example 32 includes the method of one or any combination of Examples 26-31 and optionally wherein forming the magnetic sensor includes forming the surface having an aspect ratio of approximately less than two.

Example 33 includes the method of one or any combination of Example 26-32 and optionally wherein the second binding partner corresponds to a sample under test.

Example 34 includes the method of one or any combination of Example 26-33 and optionally wherein the output corresponds to a measure of competition between second binding partners coupled to the nanofabricated particle and second binding partners free of coupling with a nanofabricated particle.

Example 35 includes the method of one or any combination of Example 26-34 and optionally wherein the output corresponds to a measure of a number of nanofabricated particles coupled to the surface.

Example 36 includes a device having a sensor and a pair of electrodes. The sensor has a surface. The surface includes a plurality of conductive layers interspersed by a plurality of intermediary layers. A magnetization direction of a first subset of the plurality of conductive layers and a magnetization direction of a second subset of the plurality of conductive layers having a ground state orientation of approximately 0 degrees. The first subset is exclusive of the second subset. An electrical resistance between the pair of electrodes is determined by a magnetic field proximate the sensor.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 1 illustrates a schematic of a system, according to one example.

FIGS. 3A, 3B, and 3C illustrate examples of detection using nanofabricated particles.

DETAILED DESCRIPTION

Part 1

Figure 2A:
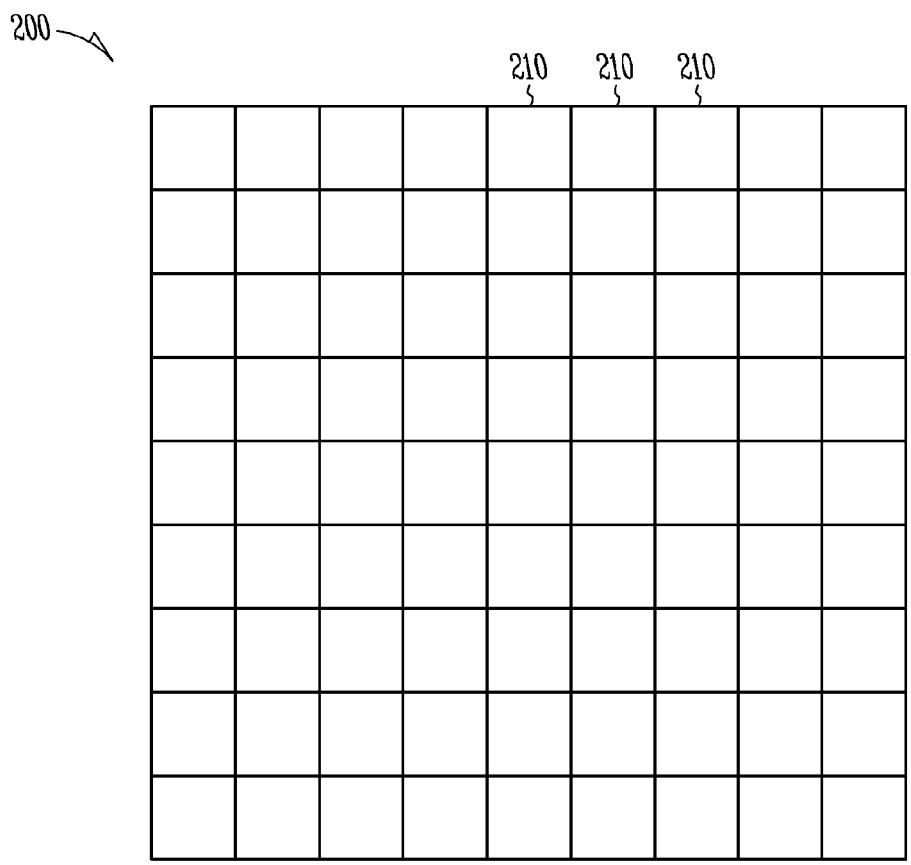
FIG. 2A illustrates a schematic of a sensor array, according to one example.

FIG. 1 illustrates a schematic of system 100 including sensor 110 and field magnet 130. Field magnet 130 provides a bias for sensor 110. Field magnet 130 represents an example of one type of magnetic field generator and other types of magnetic field generators can also be used, including an electromagnet or a permanent magnet. Sensor 110, in the example shown provides an electric signal on nodes 125 corresponding to a change in magnetic field 135 proximate to sensor surface 115. The electric signal can include a voltage, a current, a resistance, or any other electrical parameter.

In one example, sensor 110 receives an input (applied to nodes 125) such as an electric current through sensor 110. The current is modulated based on the sensed magnetic field. Switch 111 includes an electrical switch to control sensor 110. In one example, switch 111 controls electrical power delivered to sensor 110. Switch 111 can include a CMOS transistor to turn on or turn off sensor 110.

As shown in FIG. 1, magnetic field 135 has an alignment determined by field magnet 130. According to one example, surface 115 of sensor 110 includes binding partner 120. Binding partner 120, sometimes referred to as capture biomolecule (e.g. antibody), is configured to immobilize (or capture) a corresponding element in a lock-and-key manner.

In the example shown, nanofabricated particle 145 is coupled to binding partner 140. In some examples, binding partner 140 is referred to as a detection antibody. In the example shown, binding partner 140 is coupled to antigen 150. Antigen 150 is the antigen of interest and can include a biomolecule such as a protein to be detected. In some examples, antigen 150 includes binding partner 140.

Nanofabricated particle 145 can include a high magnetic moment material such as FeCo, FeCoN, FeSi, FeC, FeN, combinations of Fe, N, C, Si, and others.

Sensor 110 can include a giant magnetoresistive (GMR) sensor, a magnetic tunneling junction (MTJ) sensor, or an anisotropic magnetic (AMR) sensor, a giant magneto inductance (GMI) sensor, a Hall magnetic sensor, a magneto-optical sensor, or other sensor that provides an electrical output based on a change in magnetic field. A GMR sensor, for example, includes a layered structure. One layer, sometimes described as pinned, is separated from another layer (sometimes described as free, by an intermediary layer that can include an insulator or a conductor. In one example, a sensor includes a plurality of conductive layers interspersed (or interwoven) by a plurality of intermediary layers.

Figure 2B:
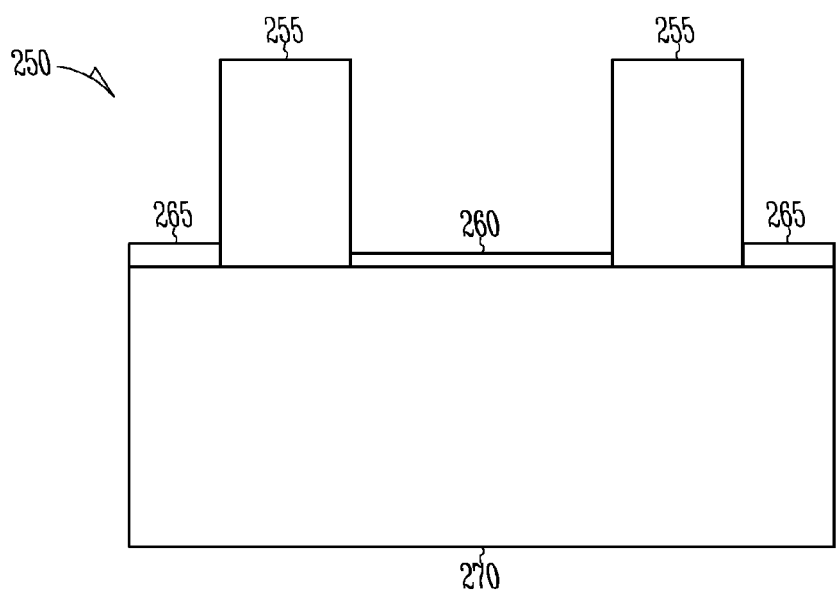
FIG. 2B illustrates a schematic of a cell of a sensor array, according to one example.

System 100 illustrates a schematic of a single nanofabricated particle 145 at a time when the nanofabricated particle 145 is near, but not bound to binding partner 120. In some examples, sensor 110 is configured to provide an output signal based on one or more detected nanofabricated particles. The nanofabricated particles may be different, similar, or matching. For example, FIG. 2A illustrates a schematic of sensor array 200. Sensor array 200 includes a plurality of cells, and in the figure, three marked examples are shown, each of which is described as cell 210. A particular cell 210 can have functionality and sensitivity that is different from all other cells in array 200 or a particular cell 210 can have functionality and sensitivity that substantially matches one or more other cells in array 200. A first cell 210 can be configured to detect a first nanofabricated particle and a second cell 210 can be configured to detect a second, and different, nanofabricated particle FIG. 2B illustrates a side view of a schematic of particular cell 250 of a sensor array. In the figure, sensor 270 includes surface 260 and nodes or electrodes 265. Electrodes 265 provide an electrical signal based on a change in magnetic field detected proximate to surface 260, and in one example, electrodes 265 can include pins on a chip, which is removable from the integrated detection system. In the example shown, reservoir walls 255 contain a liquid sample in a region near surface 260. A plurality of sensors (such as that shown in FIG. 2A) can be responsive to a single well (surrounded by walls). Sensor 270 includes a pair of electrodes.

Figure 3C:
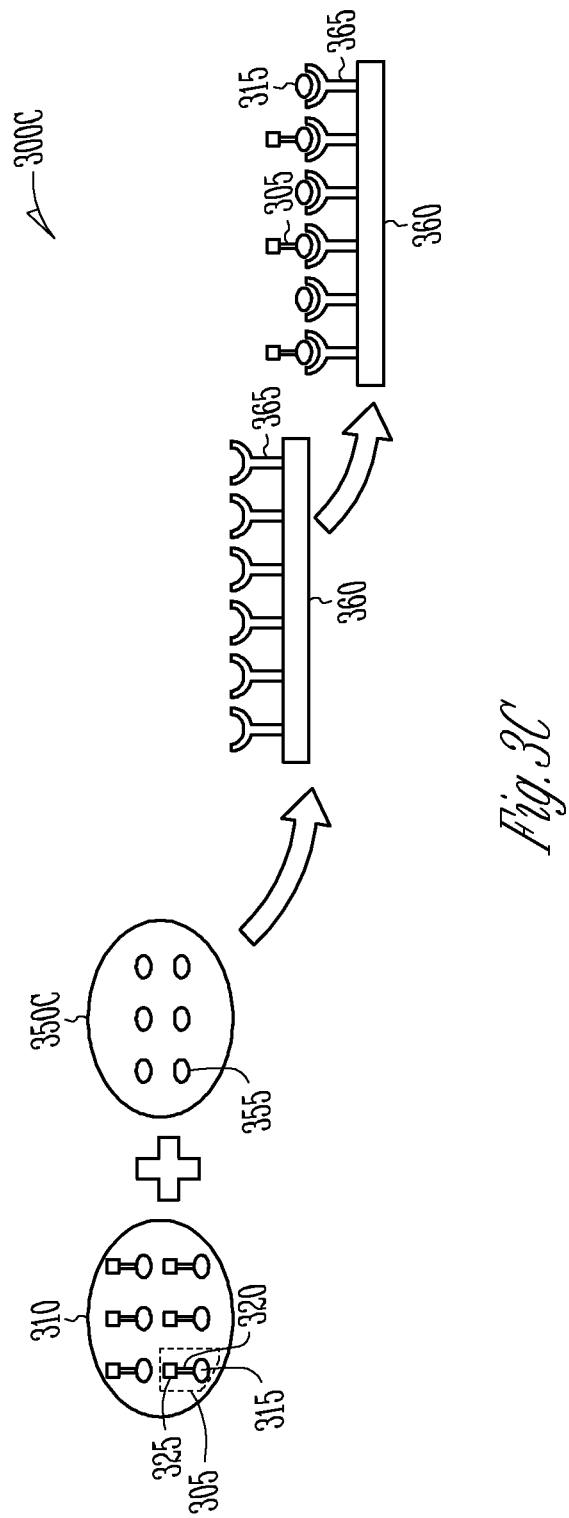

FIGS. 3A, 3B, and 3C illustrate detection based on competition using nanofabricated particles. In competition-based detection according to one example, a nanoparticle is bound to an antigen of interest in the reagent and the serum sample may include the same antigen of interest (or an antigen with the same binding properties). A capture antibody is deposited on a surface of the sensor and is configured to capture either the antigen of interest in the sample or the antigen of interest (with a bound nanoparticle) from the reagent. A measure of bound antibodies allows detection and quantification of the antigen of interest in the serum sample.

Samples 350A, 350B, and 350C represent the fluid undergoing testing and can include serum (such as blood) or other bodily fluid (such as blood, urine, exudates, lung or nasal fluid). Reagent 310 includes the nanofabricated particles which, when bound to an antigen on the surface, can be detected as a change in magnetic field.

FIG. 3A illustrates an example of system 300A in which reagent 310 includes a plurality of bound nanofabricated particles 325 and in which sample 350A has no corresponding elements. In this example, each nanofabricated particle 325 is coupled by binding partner 320 with antigen 315. A combination of a nanofabricated particle 325, binding partner 320, and antigen 315, is referred to as an element 305. Nanofabricated particle 325 can include, for example, a high-magnetic moment FeCo nanoparticle. Nanofabricated particle 325 can be fabricated using various techniques, including physical vapor nanoparticle-deposition. The size uniformity of a plurality of particles can be controlled to be in the range of 3 to 100 nm with a size distribution of less than 25% and in one example, the size distribution is less than 8% standard deviation, and in one example, the distribution is 5%. In one example, the nanofabricated particle has a magnetic moment greater than 100 emu/g at room temperature, such as 226 emu/g at room temperature. A magnetic moment greater than 100 emu/g at room temperature can be construed as a high magnetic moment. In one example, the particles have a magnetic moment that is seven times greater than that of magnetic oxide nanoparticles at 10 Oe magnetic field.

FIG. 3A also illustrates sensor 360 having six binding partners 365 followed by a view showing the six binding partners 365 bound to an equal number of elements 305.

FIG. 3B illustrates example system 300B in which reagent 310 includes a plurality of elements 305 and sample 350B having three antigens 355. As in the previous example, elements 305 each include high-magnetic moment FeCo nanofabricated particles 325 coupled by binding partner 320 with antigen 315. The figure also illustrates sensor 360 having six binding partners 365 followed by a view showing four binding partners 365 bound to an equal number of elements 305 and two binding partners 365 bound to an equal number of antigens 315.

FIG. 3C illustrates an example system 300C in which reagent 310 includes a plurality of elements 305 and sample 350C having six antigens 355. As in the previous example, element 305 each include high-magnetic moment FeCo nanoparticles coupled by binding partner 320 with antigen 315. The figure also illustrates sensor 360 having six binding partners 365 followed by a view showing three binding partners 365 bound to an equal number of elements 305 and three binding partners 365 bound to an equal number of antigens 315.

In competition detection, the capture antibody is bound to the surface of the sensor. A sample under test, along with a reagent having high magnetic moment nanofabricated particles, is exposed to the capture antibody bound to the surface of the sensor. The portion of the sample bound to the nanofabricated particles is detected using the sensor. The output signal provided by the sensor corresponds to detection of the high magnetic moment nanofabricated particles. An inverse relationship exists between the relative proportion of antigens of interest in the sample and the nanoparticle-tagged antigens in the reagent. In particular, the fewer elements 305 that are detected, then the greater the number of the antigens 355. As such, the sensor provides a signal corresponding to a ratio of nanoparticle tagged and untagged antigens. For example, detection of antigen or antibodies can be performed by determining the relative proportion of captured antibodies that are tagged with nanofabricated particles and untagged antigens present in a sample fluid.

The present subject matter can be used for disease or pathogen detection based on the principle of specific interactions between oligonucleotides, such as DNA-DNA or RNA-RNA interaction, small-molecule-biomolecule interaction, aptamer-biomolecule interactions, protein interactions, and others.

Various types of interactions can be used in the present subject matter. As noted, antibody-antigen interaction is one example of a specific interaction between biomolecules which can be used. Other examples of biomolecule interactions, include those interactions between oligonucleotides, such as DNA-DNA or interaction, small-molecule-biomolecule interaction, aptamer-biomolecule interactions and protein interactions.

For infectious diseases, DNA from virus, bacteria, or other pathogens can provide a unique biomarker for these diseases because of their unique DNA sequences. By determining the DNA sequence, the present subject matter can be used to establish detailed information regarding the disease, including the type of infectious agents and the specific strains, e. g. whether mutated or not and if mutated, what mutated strains. DNA can form double strands that are complementary to each other. One strand can be printed on a GMR sensor and the complementary strand can be labeled with a nanoparticle (the particle can be site-specifically labeled on the DNA strand to tailor the sensitivity and specificity, for instance, to label at one end of the DNA to ensure that the nanofabricated particle is positioned near the GMR sensor to increase sensitivity). DNA hybrid specific to various infectious diseases can be prepared following procedures based on cycling probe technology. DNA from a body fluid of an individual to be tested, which may contain DNA from infectious pathogen, can be incubated with DNA hybrids to form double-stranded DNA, leading to specific cleavage of DNA hybrid and production of short-piece DNA. Such short-piece DNA can compete with nanoparticle-labeled DNA, leading to signal decrease, establishing the presence of a specific DNA corresponding to a specific pathogen. This provides information regarding the nature of the infectious disease.

Certain diseases, such as drug-resistant infectious disease, can be detected based on small-molecule-biomolecule interactions. For instance, vancomycin can form specific interactions with vancomycin-resistant infectious pathogens, such as VRE and MRSA. These resistant strains can be detected based on such interaction using the present subject matter. In one example, vancomycin is attached on a GMR sensor and labeled with its specific-interaction protein/peptide with nanoparticle. Such interaction can be interrupted upon the addition of the specific pathogens, which may be present in patients, food, water, and other samples of interests, leading to the detection of such a strain.

In addition, the present subject matter can be used for disease detection using aptamer-biomolecule interactions and other types of interactions.

Figure 4A:
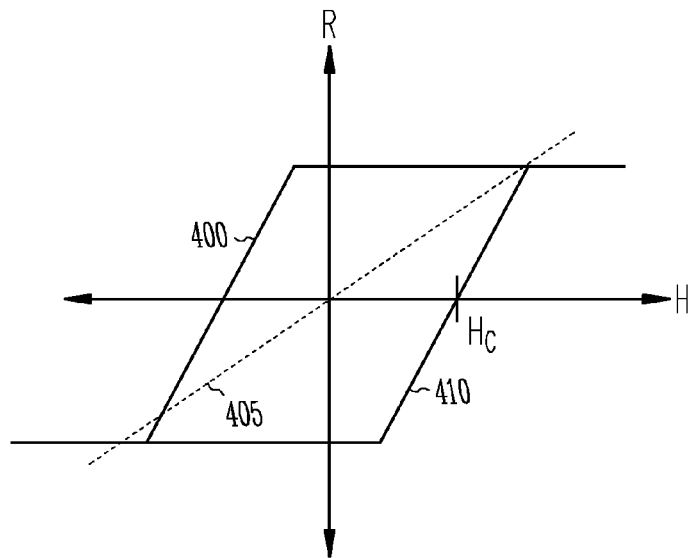
FIG. 4A illustrates a hysteresis loop, according to one example.
Figure 4B:
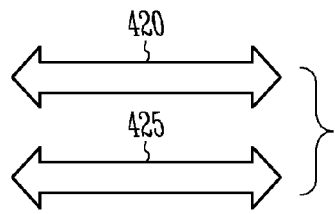
FIGS. 4B and 4C illustrate examples of magnetic field alignment.

FIG. 4A illustrates hysteresis loop 400. Loop 400 is projected on an orthogonal axis having resistance (R) and magnetic field (H). In one example, R represents a normalized electrical resistance and H represents a normalized magnetic field. Saturation occurs both at a sufficiently positive high magnetic field value and a sufficiently negative high magnetic field value. As shown in FIG. 4A, hysteresis loop 400 exhibits a slope at region 410 that exceeds the slope of line 405. Loop 400 corresponds to alignment of a magnetic moment (or magnetization) as shown in FIG. 4B. In FIG. 4B, a magnetic moment (or magnetization) of a pinned layer 425 is substantially parallel or substantially anti-parallel with a magnetic moment (or magnetization) of an unpinned (free) layer 420. Stated differently, the magnetic direction has a ground state that is substantially parallel or antiparallel and corresponds to an angular difference of near zero. The near zero ground state configuration provides a sensor having sensitivity (dR/dH) greater than that of a sensor having a 90 degree configuration. Magnetoresistive (MR) ratio is a measure of sensitivity and, in one example, is about 2.9% with a maximum sensitivity of 0.29 Ohm/Oe at 10 Oe field.

Figure 4C:
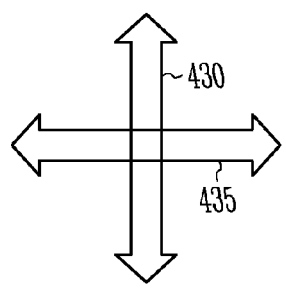

For contrast, line 405 of FIG. 4A represents a magnetic sensor configured with a pinned and unpinned layer in orthogonal alignment (as shown in FIG. 4C) and in which hysteresis is absent. In FIG. 4C, a magnetic moment (or magnetization) of a pinned layer 435 is orthogonal with a magnetic moment (or magnetization) of unpinned layer 430.

In FIG. 4A, loop 400 includes a coercivity force ($H_c$) having a value in the range of 0-1000 Oe. In one example, the sensor is sensitive to a magnetic field in the range of 0-1000 Oe with lower ranges suitable for use in biological applications and the higher ranges suitable for use in certain environmental monitoring and military applications. In one example, $H_c$ is in the range between 5 and 100 Oe.

Figure 5:
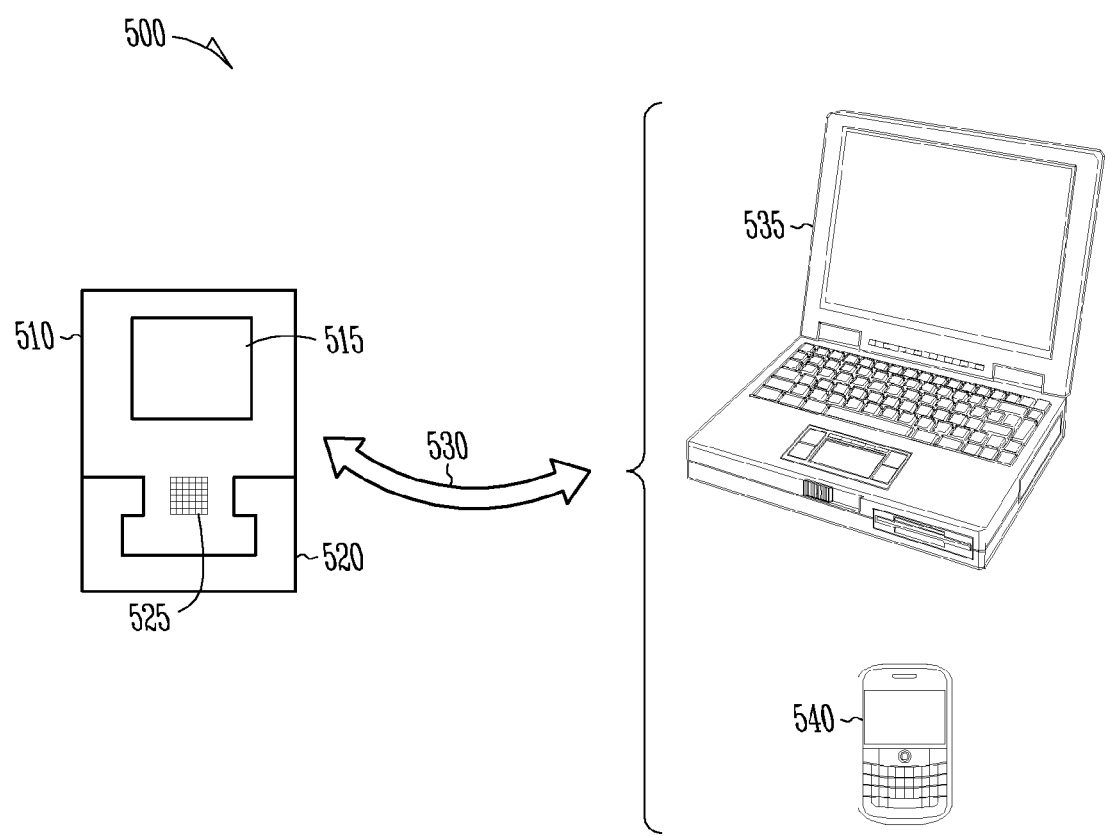
FIG. 5 illustrates a sensor system, according to one example.

FIG. 5 illustrates system 500. System 500 includes sensor module 510 having magnet 520 and sensor 525. Sensor 525 includes a multi-well plate. Sensor module 510 includes circuitry 515 configured to communicate with a user interface. In the example illustrated, sensor module 510 communicates using data channel 530 with computer 535 or handheld device 540. Computer 535 can include a desktop, a laptop, a mobile phone processor based machine, a server, or other processor based device and suitable for use in a clinical facility, a medical facility, or a household. Computer 535 can include a mobile device coupled to a communication network such as the internet or a local area network. Any combination of module 510, computer 535, or handheld device 540 can include a display to provide alphanumeric or graphical data. Module 510 can include a data transfer module to allow interfacing with a remote device (such as a computer or a handheld device) using a wired or wireless channel.

In various examples, circuitry 515 is configured to control the magnetic field and to switch on and off the current flowing through the sensor. In addition, circuitry 515 can be configured to collect data and communicate with a user interface.

System 500 can include additional circuits or elements as well. For example, an amplifier or filter can be provided to process the signal from the sensor. In addition, system 500 can be configured to modulate the magnetic field.

In various examples, communication data channel 530 is configured to transfer the data from system 500 to the processor 535 and send back the control signal from the computer 535 to the system 500. In addition, channel 530 can be wireless such as Bluetooth technology or USB connection or other format of system and computer connections.

A multi-well plate, sometimes referred to as a microplate, a microtiter plate or a well plate, is a flat plate with multiple wells or reservoirs used as small test tubes. A microplate typically has 6, 24, 96, 384 or more sample wells arranged in a matrix. Each well typically holds somewhere between tens of nanoliters to several tens of milliliters of liquid or dry powder. The wells (or container) can be circular, square, rectangular, or another shape and can be configured to receive a sample bodily fluid. In various examples, the wells can have dimensions of 1 mm to 15 mm. The wells can be fabricated of polydimethylsiloxane (PDMS) or other polymer.

In one example, a microfluidic channel carries the sample under test to a region near the sensor surface. The microfluidic channel can include a valve, a pump, a vent, a reservoir, or other elements.

In one example, handheld device 540 is configured for patient use in a household or configured for use in a clinical setting.

Data channel 530 can be unidirectional or bidirectional and in various examples, includes a wired (such as a USB connection) or wireless connection (such as a Bluetooth connection).

Part 2

The present subject matter includes systems and methods that can provide infection detection, diabetes detection and monitoring, heart attack monitoring, early chronic disease detection, biomarker searching and verification, efficacy of therapies confirmation and post-therapy (recurrence) monitoring. In addition to these and other applications, the present subject matter can be used for environmental monitoring.

Longitudinally monitoring of changes in protein biomarkers (generally less than one pmol) may enable effective treatment for a specific individual and early detection of chronic diseases. Such an approach can be used for personalized medicine and control of chronic diseases.

The present subject matter includes a low cost detection system that can be compatible with current electronic technologies. Using a spintronic sensor and magnetic nanoparticle labeling, an example of the present detection and quantification system includes a highly-sensitive giant magnetoresistive (GMR) chip and approximately 12 nm high-magnetic-moment FeCo cubic nanoparticles. The nanoparticles can be of different nominal size, including 10-15 nm. The system can demonstrate linear detection of 300-6000 copies of streptavidin within minutes. Because of the magnetic and electric nature, the system can be integrated with current electronic technologies and configured to communicate with a computer (such as a laptop), a handheld computing device, or a cellular telephone. The present system may quantify potential biomarkers from 10 nl or less of body fluids. A sensor other than a GMR magnetic sensor can be used, including a magnetic tunneling junction sensor, an anisotropic magnetoresistive sensor, a Hall sensor, a giant magneto-impendence sensor, and others.

In one example, a personalized medical device can be used for family-based early chronic disease detection. For instance, the device can be used for early detection of lung cancer. One or more elements can be configured as disposable elements.

In one example, a clinic-based medical device can be used for early chronic disease detection. For example, early stage cancer can be detected using one embodiment. A clinic-based medical device can be suitable for use in a developing country.

An example of the present subject matter can include a research tool having an integrated system suitable for searching and mapping biomarkers for various chronic diseases.

Changes in a magnetic field can be detected using a magnetoelectronic sensor, including a giant magnetoresistive (GMR) sensor. A GMR sensor can detect magnetic stray fields resulting from magnetic labels on or near the sensor surface.

A magnetic biosensors can detect biomolecules with relatively large particle labels (>250 nm). The high mass and size of the label in relation to biomolecules to be tethered may interfere with the natural biomolecule movement, recognition, and binding, which may not be important with small-sized magnetic nanoparticles.

Magnetic nanoparticles, on the other hand, as detectable labels, acquire a smaller magnetic moment than larger ones. Greater sensitivity can provide more accurate results. The present subject matter concerns using small magnetic nanoparticles for sensitive detection and quantification of biomolecules.

Part 3

An example of the present system provides sensitivity sufficient to detect $10^{-21}$ moles of biomolecules. In this example, the signal can be used without amplification in order to improve the detection limit.

According to one theory, sensitivity is improved based on the ultra sensitive detection method and based on the high-magnetic-moment nanoparticles.

The nanoparticles used in one example of the system are 12 nm in length. This dimension is smaller than magnetic nanotags (MNTs) and other magnetic particles used in GMR biosensing. A small-sized magnetic labeling enables biological application.

In addition, the nanoparticles of the present system are highly homogenous and exhibit little or no aggregation.

One example provides that each nanoparticle is modified by one streptavidin molecule (or IL-6).

The present subject matter exhibits a linear dose-response curve based on the amount of biomolecules. The linear curve of the present subject matter corresponds to the improved sensitivity and can provide three decades of detection range.

An example of the present system can be embodied as a hand-held working device and testing electronic chip.

In one example, the biomarkers are detected by a competition-based algorithm.

Part 4

In one example, a GMR chip is functionalized with a capture antibody for a particular antigen and the nanoparticles are functionalized with a detection antibody. The magnetic nanoparticles serve as a tag to identify the presence of an antigen by altering the magnetic field in the presence of the GMR sensor. The high magnetic moment nanoparticles are attached to an antigen of interest that is introduced to the GMR sensor along with the sample fluid. The antigens attached to the nanoparticles and the antigens in the sample fluid compete for capture antibodies. Detection of antigens or antibodies is performed by determining the relative proportion of captured antigens that are tagged with nanoparticles and antigens present in the sample fluid. The GMR sensor design uses hysteresis resulting from a free layer substantially parallel with a pinned layer in order to provide high sensitivity.

The GMR sensor can be attached to a sandwich-based assay or a bi-layer competition-based assay. An example of a competition-based assay is shown in FIGS. 3A, 3B, and 3C. The sandwich based assay includes a first capture antibody attached to the GMR sensor and a second detection antibody that serves as a tag. The bi-layer competition-based assay uses a single antibody attached to the GMR sensor.

Part 5

The following section concerns a competition-based nanomagnetic quantification of biomarkers in sera for early disease detection. The present subject matter includes longitudinal monitoring of biomarker changes in a non-clinical setting.

One example includes a giant magnetoresistive (GMR) biosensor and high magnetic moment nanoparticle-based detection. The magnetic bias field can be approximately 10 Oe for detecting human Interleukin-6 (IL-6) in unprocessed human serums. At such a field, normal individuals can be differentiated from lung cancer patients. Detection of IL-6 levels as low as 150 molecules can be demonstrated using 4 nL unprocessed serum in 5 minutes.

The present subject matter can monitor a cancer biomarker level using a droplet of body fluid (e.g. blood or urine).

A GMR-based sensor can be portable and low cost, and may offer rapid detection and compatibility with silicon IC technology, ease of integration into lab-on-chip systems, and high signal to noise ratio due to the low magnetic background in a biological sample.

One example includes a GMR biosensor operable with a magnetic field of 1-15 Oe DC. Unlike commercial iron oxide, superparamagnetic particles having low magnetic moment and high size variation (50 nm to 3 μm), the present subject matter uses a nanofabricated particle having a high magnetic moment and high homogeneity.

High magnetic moment nanoparticle can provide enhancing diffusivity and binding efficiency. An example of the present subject matter includes highly homogeneous sub-13 nm high moment FeCo superparamagnetic nanoparticles. Other examples in addition to iron oxide can include cobalt oxide or ferrite nanoparticles. Examples of high moment nanofabricated particle candidates include Fe, Co, FeCo, FeCoN, FeN, $Fe_{16}N_2$, MnN, and others.

The nanofabricated particles can have a heterostructured (or hybrid) structure. For example, the particle can have a core surrounded by a shell. The core can include a material such as Au, Ag, SiO, C, MgO, or Ca or other magnetic metal core. A first part of the particle can include Au, Ag, $SiO_2$, C, MgO, Ca or other biocompatible materials and a second part of the particle can include a magnetic material.

Homogeneity can refer to a standard deviation as to a measure of volume for the particles, a length (such as an edge) of the particles, a length of a cube, an average diameter of particles. Homogeneity can be quantified as a standard deviation less than a particular value such as less than 50%, less than 30%, less than 15%, or less than 5%.

One example includes a GMR biosensor and 12.8 nm high-moment FeCo magnetic nanoparticle for the quantification of human IL-6 molecules in 4 nl serum sample. Such a device can be used to longitudinally monitor molecular changes indicative of chronic diseases in a personalized setting and providing early detection of chronic diseases. The device can include reaction wells on a replaceable chip containing GMR biosensors for multiplex detection, on-board signal acquisition and data processing electronics and a current driven electromagnet. The electromagnet can be part of a magnetic field generator module and configured to generate a magnetic field. The magnetic field generator can be coil-based, electromagnet-based, or permanent magnet-based.

In one example, the magnetic field generator module is configured to generate two or more fields. The fields can have a frequency ranging from DC to 1 MHz.

An example of a medical device includes (a) reaction wells on a replaceable chip containing GMR biosensors for multiplex detection, (b) on-board signal acquisition and data processing electronics and, (c) a current driven electromagnet. Each replaceable chip has six reaction wells. For multiplex detection, each reaction well is pre-coated with different capture antibodies specific to respective biomarkers. Human body fluid sample (e.g. blood, urine) can be spotted into the reaction wells for different biomarkers quantification. In the reaction well, GMR biosensor arrays are covered by a thin SiO2 layer which is suitable for surface functionalization. The GMR biosensors includes the following multilayer structure: Ta (5 nm) $Ir_{0.8}Mn_{0.2}$ (10 nm)/$Co_{0.9}Fe_{0.1}$ (2.5 nm)/Cu (3.3 nm)/$Co_{0.9}Fe_{0.1}$ (1 nm)/$Ni_{0.82}Fe_{0.12}$ (2 nm)/Ta (5 nm), deposited on thermal oxide silicon wafer using a six-target shamrock sputtering system. An antiferromagnetic layer $Ir_{0.8}Mn_{0.2}$ layer can be used to pin the fixed magnetic $Co_{0.9}Fe_{0.1}$ layer. The free layer includes $Co_{0.9}Fe_{0.1}$ and $Ni_{0.82}Fe_{0.12}$ bi-layers, which is very sensitive to the external magnetic field. The GMR multilayer film can be patterned into rectangular shape with a size of 80 μm×40 μm using photolithography, electron beam lithography, or an ion milling technique. Corrosion resistant electrode leads can be passivated with an additional 1 μm thick $SiO_2$ layer. Since only a small working magnetic field is needed, an on-board electromagnet can be used. The amplitude and polarization of the magnetic field can be controlled by the on-board electronics. One example uses a micro-controller and digital signal processing units.

With dimensions of 80 μm×40 μm, the aspect ratio of length to width can be represented as having a value of 2. Other aspect ratios are also contemplated including, for example, 100 or less, or 10 or less. In one example, the sensor has a length that differs from the width.

One methodology for the GMR biosensor and magnetic nanoparticle-based detection scheme is the sandwich approach which uses at least two antibodies for a target analyte. According to the sandwich approach, the GMR biosensors are functionalized with capture antibodies specific to an analyte. The analyte are then spotted onto the sensor surface and captured. Subsequently, the MNL detection antibodies are then applied and bind to the captured analyte. The sensor can be functionalized by printing a binding partner.

Another method for the sensor can be referred to as a competition, or bi-layer approach. In such an approach, after the functionalization with capture antibodies, the magnetic nanoparticle modified analyte are directly applied and captured on the sensors.

The bi-layer approach uses one antibody and provides greater sensitivity over the sandwich approach. The sandwich approach includes the following: the GMR biosensors are first functionalized with capture antibodies specific to the analyte; then analyte are applied onto the GMR biosensor and followed by the magnetic nanoparticle labeled (MNL) detection antibodies; finally, the analyte are sandwiched by the capture antibody and MNL detection antibody. By detecting the bound magnetic nanoparticles by GMR biosensor, the captured analyte can be quantified.

The bi-layer approach uses the direct application of MNL analyte onto the capture antibody modified sensor. Although based on different modification steps, these two approaches share the same magnetic nanoparticle detection principle.

Under either the sandwich or bi-layer approach, the MNL analyte are attached to the sensor surface. The magnetic dipole field $H_{dip}$ of the superparamagnetic nanoparticle can be modeled as:

$$H_{dip} \propto \frac{m}{r^3}$$

where r is the distance between the center of superparamagnetic nanoparticle to the point where the field is measured, $m = V\chi H_a$ is the magnetic moment of the superparamagnetic nanoparticle under the applied field $H_a$, V is the volume of the superparamagnetic nanoparticle and $\chi$ is the susceptibility of the superparamagnetic nanoparticle. Because the resistance of GMR biosensor responds easily to the in-plane magnetic field, the magnetic dipole field from the nanoparticle bound to the surface can be detected by the GMR biosensor. Since the dipole field is much smaller than that with the applied field, assume a linear relationship between the resistance R and the effective magnetic field:

$$R = C \cdot H_{eff}$$

where C is a coefficient. For a bare GMR sensor, the effective magnetic field on the sensor is just the applied field. So the resistance of the sensor $R_0$ in this case is:

$$R_0 = C \cdot H_a$$

After the nanoparticle attachment, the effective magnetic field on the sensor, considering the dipole field from the nanoparticles, is $H_{eff} = H_a - H_{dip}$. Hence, the resistance of the sensor $R_1$ is:

$$R_1 = C \cdot H_{eff}$$
$$= C \cdot (H_a - H_{dip})$$

Therefore, the sensing signal S is defined as the resistance difference with and without nanoparticle attachment:

$$S = R_0 - R_1$$

-continued $$= C \cdot H_a - C \cdot (H_a - H_{dip})$$

$$= C \cdot H_{dip}$$

Using a potential serum biomarker for lung cancer, the sensitivity of both sandwich and bi-layer approaches can be compared. According to one example, as few as $5 \times 10^4$ IL-6 molecules can be detected a sandwich approach, while bi-layer approach increases the sensitivity of this system down to 900 IL-6 molecules, which is 55 times more sensitive to the sandwich approach. The sensitivity increase in bi-layer case may be related to smaller distance between the magnetic nanoparticles and the GMR biosensor.

A bi-layer approach provides high sensitivity but may entail labeling the IL-6 in the biological sample with magnetic nanoparticle. To quantify IL-6 from biological sample directly, one example uses the bi-layer based competition detection approach. The dose response curve of the competition detection approach provides a dynamic detection range from 100 to $10^6$ unlabeled IL-6 molecules.

An example of the present subject matter includes an ultra-sensitive and low cost family medical device based on GMR biosensor and 12.8 nm high moment FeCo magnetic nanolabels. The system can quantify human IL-6 in unprocessed human serum samples, by a competition based assay capable of differentiating normal and cancer serums. Detection of IL-6 levels as low as 150 molecules can be demonstrated using only 4 nL serum volume in 5 minutes.

Part 6

The present subject matter can include a functionalized sensor having parallel and anti-parallel layers. The sensor operates on a selected portion of a hysteresis loop. The layers are substantially parallel in orientation. In various examples, the layers are less than approximately 40° of parallel or less than approximately 60° of parallel. In one example, the layers provide hysteresis and the coercivity force is non-zero.

The shape of the sensor active area, in one example, has a low aspect ratio. A low aspect ratio is approximately less than two, such as, for example, an active area having a width of approximately 40 μm and a length of approximately 80 μm. A narrow surface area dimension will yield greater slope changes in the hysteresis loop. In one example, the pinned layer is fabricated by cooling under a magnetic field bias. The free layer is made of a particular size to yield a grain.

Part 7

Binding Partners

A binding partner is configured to bind in a manner akin to a lock and key. For example, a first binding partner can be affixed to the nanoparticle and configured to bind to the target element in the sample and a second binding partner can be affixed to the surface of the sensor.

In one example, the binding partner is configured to bind with one or more microorganisms of interest. The microorganism may be a pathogenic microorganism. For example, the binding partner can be an antibody or fragment thereof that binds to a particular analyte. In one example, the binding partner binds specifically to a particular microorganism, such as an antibody for *C. parvum*. In one example, immunocapture is used to select and concentrate the microorganism of interest from the sample.

In various examples a binding partner includes a hapten-specific, peptide-specific, or an antigen-specific antibody population. The sample fluid can be immobilized using a monoclonal antibody, a polyclonal antibody, or a binding fragment thereof. In one example, an APTase, or an RNA APTase of a microorganism of interest is used as a binding partner. In one example, the binding partner preferentially attaches to a predetermined microbe.

A sensor having a relatively large surface area can increase the likelihood of a single organism of interest contacting and binding to a binding partner.

In addition, a textured or porous surface can provide an increased area to enhance the attachment of an immobilized binding partner.

Various means can be used to immobilize the binding partner to the sensor surface or to the nanofabricated particle. For example, in one embodiment, conjugate pairs can be used. Other means of immobilizing the binding partner are also contemplated, including chemical bindings, such as esterification, amide formation, carbamate formation, and non-chemical bindings such as hydrophobic interactions.

The immobilized binding partner can include a biofilm selected to bind with a particular substance in a "lock and key" fashion. A portion of the surface can be coated with a biofilm. The biofilm can be installed by means of capillary action in a manner akin to the installation of a sample fluid. The biofilm binds with a particular target substance. In various embodiments, the biofilm may bind with one or more targeted substances.

The biofilm, having one or more binding partners, may be selected to bind to a desired target substance, or substances. In one example, one protein (such as an antibody) may be used as a binding partner for purposes of detecting a second protein (such as an antigen). By way of example, other combinations include using a receptor for detecting a ligand (such as using a cellular receptor to identify a ligand that binds to the receptor), using a protein for detecting a peptide, using a protein for detecting a DNA, using a first DNA sequence to detect a second DNA sequence, using a metallic ion to detect a chelator, and using an antibody (or an antibody fragment), for detecting an antigen or analyte.

In various examples, the binding partners bind to each other in a "lock and key" fashion by ionic bonding, covalent bonding or a combination thereof. In some examples, the binding partner can bind specifically to a single target substance or subunit thereof. As such, either the "lock" can be immobilized on the surface of the sensor or on the nanofabricated particle for detecting the "key" or alternatively, the "key" can be immobilized on the surface of the sensor or on the nanofabricated particle for detecting the "lock." As an example, a peptide may be the binding partner for use in detecting a protein. The binding partner can be DNA and thus, the present system is responsive to the substantial DNA complement. The bound, or "hybridized" DNA sequences can then be treated or "washed" under various conditions of stringency so that only DNA sequences that are highly complementary (e.g., that has high sequence identity) will be retained.

The binding partner can also bind to a plurality of substances. In addition, more than one binding partner can be immobilized in a particular example to enable detection of multiple molecules. Multiple binding partners may be immobilized in the same or different regions of the surface of the sensor or on different nanofabricated particles.

The binding partner can include an antibody for detection of an antigen, or binding partner includes an antigen for detection of an antibody. Examples of antigens include proteins, oligopeptides, polypeptides, viruses and bacteria. For instance, antigens include OMPa, OMPb and OMPc, commonly referred to as outer membrane protein "a" "b" and "c," respectively. In such cases involving antigens, the interaction includes one or more amino acid interactions wherein the amino acids are spatially arranged to form two complementary surfaces in three dimensions. Each surface includes one or more amino acid side chains or backbones.

The binding partner can include an antibody for detection of a hapten, or the binding partner can include a hapten for detection of an antibody. Haptens tend to be much smaller than antigens and include such compounds as transition metal chelators, multi-ring phenols, lipids and phospholipids. In such cases involving haptens, the interaction includes an intermolecular reaction of a surface of the hapten with one or more amino acids of the antibody, wherein the amino acids of the antibody are spatially arranged to form a complementary surface to that of the hapten.

The interaction between amino acids, such as antibody-antigen or antibody-hapten, arises by van der Waal forces, Lennard-Jones forces, electrostatic forces or hydrogen bonding. Consequently, immobilized binding partner interacts with the targeted substance in a manner beyond that of simple absorption of analyte into a matrix of some type. The interaction of binding partner with the target substance can include rapid bonding that is typically irreversible under ambient conditions, thus reducing the time for reliable detection.

Hybrid antibodies are contemplated for either the target substance or binding partner. For example, a portion of a first antibody may be cleaved and a second antibody may be bonded to the remaining portion of the first antibody, thus forming a hybridized antibody. Such an antibody may subsequently bind with two forms of antigens or haptens. As yet another example, a third antibody may be bonded to the remaining portion of the first antibody, thus enabling subsequent bonding to additional antigens or haptens. The use of hybridized antibodies can yield a detector sensitive to multiple substances and may be desirable for certain applications involving two or more analytes.

The binding partner may be affixed, or immobilized, using any of a number of techniques, including absorption, covalent bonding with or without linker or spacer molecules or complexation.

The present subject matter can be configured to operate using various binding partners. For example, a binding partner can include an immobilized monoclonal antibody, a polyclonal antibody, or a binding fragment thereof, that binds to the target microorganism.

In addition, the binding partner can include an immobilized APTase, RNA APTase, or binding fragment thereof, that binds to the target microorganism.

A binding partner can selectively bind to a component of a microorganism.

In one example, the binding partner includes a population of antibodies.

In one example, the sensor is configured to include one or more notches at the perimeter of the layer or at a location within the perimeter (i.e., inside the perimeter). A notch is configured to pin the magnetization of the layer. The notch can include a void or it can include an inclusion that is of a different material than the conductive layer. Ordinarily, defects or voids (such as a notch) will damage a linear response curve for a sensor having a 90 degree ground state. A defect or void will cause coercive field for the transfer curve. A notch, for example, may improve the stability of the sensor having a near 0 degree ground state and thus improve the reliability and the signal to noise ratio.

Figure 6B:
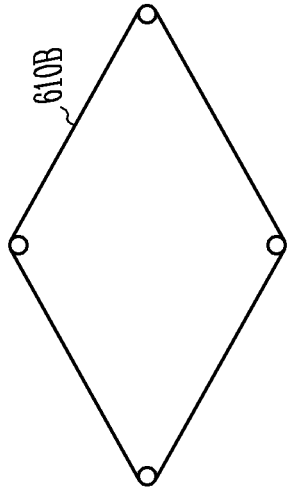
FIGS. 6A, 6B, 6C, and 6D illustrate sensor surfaces, according to various examples.
Figure 6D:
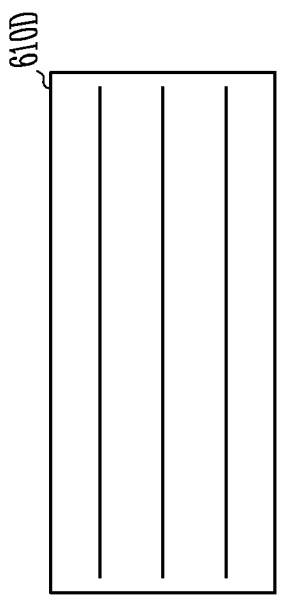
Figure 6A:
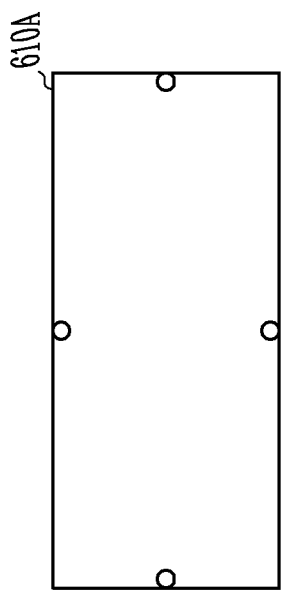
Figure 6C:
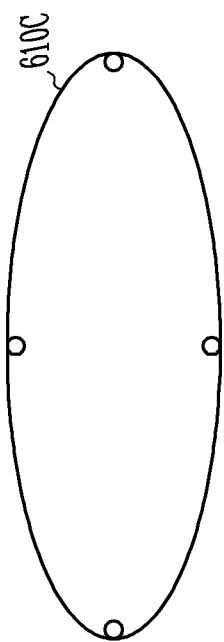

FIGS. 6A, 6B, 6C, and 6D illustrate sensor surfaces having features including notches and line-types, according to various examples. FIG. 6A illustrates surface 610A having a rectangular planform and notches disposed along the sides. FIG. 6B illustrates surface 610B having a diamond-shaped planform and notches disposed at the corners. FIG. 6C illustrates surface 610C having an oval or elliptical planform and notches uniformly disposed about the perimeter. FIG. 6D illustrates surface 610D having a rectangular planform and line-type notches or grooves disposed atop the surface. A notch or similar feature can improve the uniformity (sensor to sensor), reliability and repeatability for fabricating sensors in a large wafer level later.

A variety of sensor shapes (e.g., rectangular, diamond, ellipse) and different notches configuration and location (circle, half circle, square, long lines) can be used.

In one example, a notch can be a void (material can be removed by etching with a mask) or an insert (or inclusion) that is of a different material as the sensor layer. The inclusions can be implanted or induced by a ion beam process with a mask. The notch or other feature serves to pin the magnetization along certain directions and thus form fixed multidomain structures per fabricated sensor, that is repeatable with the applied magnetic field.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile tangible computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The claimed invention is:

1. A device comprising:
a sensor surface including a first conductive layer separated from a second conductive layer by an intermediary layer, a magnetization direction of the first conductive layer and a magnetization direction of the second conductive layer having a ground state orientation of approximately 0 degrees;
a pair of electrodes coupled to the sensor surface and wherein an electrical resistance difference between the pair of electrodes is determined by a magnetic field proximate the sensor surface and wherein the sensor surface has an aspect ratio, corresponding to a length and a width of the sensor surface, that is sufficiently small such that a magnetic dipole field of a nanoparticle proximate the sensor surface is detectable as an electrical resistance difference between the pair of electrodes; and
wherein the sensor surface is configured to detect proximity of a high magnetic moment particle, and the particles have a magnetic moment that is seven times greater than that of magnetic oxide nanoparticles at 10 Oe magnetic field.

2. The device of claim 1 wherein the ground state orientation is less than 60 degrees.

3. The device of claim 1 wherein the particles have a magnetic moment greater than 100 emu/g at room temperature.

4. The device of claim 1 wherein the particles include high magnetic moment FeCo nanoparticles.

5. The device of claim 4 wherein the nanoparticles are approximately 12 nm.

6. The device of claim 1 wherein the sensor surface and the pair of electrodes are integrated in a chip.

7. The device of claim 6 wherein the chip includes a processor module configured to acquire data corresponding to the magnetic field.

8. The device of claim 1 further including a magnetic field generator module configured to generate the magnetic field.

9. The device of claim 8 wherein the magnetic field generator module is configured to generate two or more fields having a frequency in the range of 0 Hz to 1 MHz.

10. The device of claim 1 wherein the magnetic field is determined by a ratio of magnetic particle tagged binding partners to untagged binding partners.

11. The device of claim 1 wherein the sensor surface has a width of approximately 40 μm and a length of approximately 80 μm.

12. The device of claim 1 wherein the sensor surface has a ratio of length to width of less than 100.

13. The device of claim 1 wherein the sensor has a non-zero coercivity force.

14. The device of claim 1 wherein the electrical resistance as a function of the magnetic field exhibits hysteresis.

15. The device of claim 1 wherein the sensor surface includes at least one microfluidic channel.

16. The device of claim 1 wherein the sensor surface includes a container configured to receive a fluid sample.

17. The device of claim 1 wherein the sensor surface is part of at least one of a giant magnetoresistive (GMR) sensor, a magnetic tunneling junction (MTJ) sensor, an anisotropic magnetic (AMR) sensor, a giant magneto inductance (GMI) sensor, a Hall magnetic sensor, a magneto-optical sensor, or other sensor that provides an electrical output based on a change in magnetic field.

18. The device of claim 1 further including an interface to exchange data based on the electrical resistance with a remote device.

19. The device of claim 1 further including a notch in a perimeter of at least one of the first conductive layer or the second conductive layer, the notch configured to pin the magnetization.

20. A method comprising:
exposing a sensor surface to a magnetic field, the sensor surface having an aspect ratio corresponding to a length and a width;
based on the magnetic field, determining an electrical resistance difference corresponding to a change in a number of nanoparticles proximate the sensor surface, the nanoparticles having a high-magnetic moment, the number of nanoparticles corresponding to a change in magnetization alignment of a first layer relative to a second layer of the sensor surface, the magnetic field applied in a direction corresponding to a non-zero coercive force, the first layer and the second layer having a ground state of approximately zero, the aspect ratio sufficiently small to enable detection of the electrical resistance difference, and the change in magnetization alignment corresponding to a change in a hysteresis loop of the sensor.

21. The method of claim 20 further including affixing a binding partner to the sensor surface.

22. The method of claim 21 wherein determining the electrical resistance difference includes determining a ratio of magnetic particle tagged binding partners to untagged binding partners.

23. The method of claim 20 further including communicating data corresponding to the electrical resistance difference to a remote device.

24. The method of claim 20 wherein the sensor surface includes voids or inclusions configured to form a fixed multidomain structure.

25. A method of manufacturing a device comprising:
forming a magnetic sensor having a plurality of layers, at least two of which are in at least one of substantially parallel alignment and substantially antiparallel alignment, the sensor surface having a fixed multidomain structure and having an aspect ratio corresponding to a length and a width; and
immobilizing a first binding partner to a surface of the sensor, the first binding partner configured to bind to a second binding partner, the second binding partner coupled to a nanofabricated particle, the nanofabricated particle having a high magnetic moment and wherein the magnetic sensor provides an output based on detecting the nanofabricated particle proximate the surface, the aspect ratio sufficiently small to provide an electrical resistance difference corresponding to the sensor surface with the nanofabricated particle and without the nanofabricated particle.

26. The method of claim 25 wherein forming the magnetic sensor includes forming a giant magnetoresistive sensor.

27. The method of claim 25 wherein immobilizing the first binding partner includes immobilizing a capture antibody, a DNA strand, an RNA strand, a small molecule, a peptide, an aptamer, or a multiplex biomolecule to the surface.

28. The method of claim 25 wherein immobilizing the first binding partner includes immobilizing a capture oligonucleotide or polynucleotide to the surface.

29. The method of claim 25 wherein the second binding partner includes at least one of an antigen, a oligonucleotide, a polynucleotide, a pathogen, a protein, and a peptide.

30. The method of claim 25 further including providing a data communication channel between the output and a user perceivable display.

31. The method of claim 25 wherein forming the magnetic sensor includes forming the surface having an aspect ratio of approximately less than two.

32. The method of claim 25 wherein the second binding partner corresponds to a sample under test.

33. The method of claim 25 wherein the output corresponds to a measure of competition between second binding partners coupled to the nanofabricated particle and second binding partners free of coupling with a nanofabricated particle.

34. The method of claim 25 wherein the output corresponds to a measure of a number of nanofabricated particles coupled to the surface.

* * * * *

UNITED STATES PATENT AND TRADEMARK OFFICE
CERTIFICATE OF CORRECTION

| | | |
|---|---|---|
| PATENT NO. | : 9,121,887 B2 | Page 1 of 1 |
| APPLICATION NO. | : 12/712989 | |
| DATED | : September 1, 2015 | |
| INVENTOR(S) | : Wang et al. | |

It is certified that error appears in the above-identified patent and that said Letters Patent is hereby corrected as shown below:

In the Specification

In column 1, line 16, after "reference.", insert --GOVERNMENT SUPPORT
This invention was made with government support under CBET-0730825 awarded by
the National Science Foundation. The government has certain rights in the invention.--,
therefor Signed and Sealed this
Fifteenth Day of March, 2016

Michelle K. Lee
*Director of the United States Patent and Trademark Office*